United States Patent
Chen

(10) Patent No.: US 7,280,630 B2
(45) Date of Patent: Oct. 9, 2007

(54) CALCULATION OF ADDITIONAL PROJECTION DATA FROM PROJECTION DATA ACQUIRED WITH A DIVERGENT BEAM

(75) Inventor: Guang-Hong Chen, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/378,072

(22) Filed: Mar. 17, 2006

(65) Prior Publication Data

US 2006/0193429 A1    Aug. 31, 2006

Related U.S. Application Data

(63) Continuation-in-part of application No. 10/955,459, filed on Sep. 30, 2004, now Pat. No. 7,050,528.

(51) Int. Cl.
*A61B 6/00* (2006.01)

(52) U.S. Cl. .......................................... 378/4; 378/901
(58) Field of Classification Search ..................... 378/4, 378/15, 19, 207, 901
See application file for complete search history.

(56) References Cited

U.S. PATENT DOCUMENTS 7,050,528 B2 *   5/2006   Chen .............................. 378/4

* cited by examiner

*Primary Examiner*—Courtney Thomas
(74) *Attorney, Agent, or Firm*—Quarles & Brady LLP

(57) ABSTRACT

A data consistency condition is derived for an array of attenuation values acquired with a divergent beam. Using this data consistency condition, estimates of selected attenuation values can be calculated from the other attenuation values acquired during the scan. Such estimates may be used to replace corrupted data in the acquired data set, or attenuation values may be added to the acquired data set to increase in-plane resolution of a reconstructed image.

20 Claims, 6 Drawing Sheets

CALCULATION OF ADDITIONAL PROJECTION DATA FROM PROJECTION DATA ACQUIRED WITH A DIVERGENT BEAM

CROSS-REFERENCE TO RELATED APPLICATIONS

This application is a continuation-in-part of U.S. patent application Ser. No. 10/955,459 filed on Sep. 30, 2004, now U.S. Pat. No. 7,050,528, and entitled "CORRECTION OF CT IMAGES FOR TRUNCATED OR INCOMPLETE PROJECTIONS".

STATEMENT REGARDING FEDERALLY SPONSORED RESEARCH

This invention was made with government support under Grant No. 1R21 EB001683-01 awarded by the National Institute of Health. The United States Government has certain rights in this invention.

BACKGROUND OF THE INVENTION

The field of the present invention is computed tomography and, particularly, computer tomography (CT) scanners used to produce medical images from x-ray attenuation measurements.

As shown in FIG. 1, a CT scanner used to produce images of the human anatomy includes a patient table 10 which can be positioned within the aperture 11 of a gantry 12. A source of highly columinated x-rays 13 is mounted within the gantry 12 to one side of its aperture 11, and one or more detectors 14 are mounted to the other side of the aperture. The x-ray source 13 and detectors 14 are revolved about the aperture 11 during a scan of the patient to obtain x-ray attenuation measurements from many different angles through a range of at least 180° of revolution.

A complete scan of the patient is comprised of a set of x-ray attenuation measurements which are made at discrete angular orientations of the x-ray source 13 and detector 14. Each such set of measurements is referred to in the art as a "view" and the results of each such set of measurements is a transmission profile. As shown in FIG. 2A, the set of measurements in each view may be obtained by simultaneously translating the x-ray source 13 and detector 14 across the acquisition field of view, as indicated by arrows 15. As the devices 13 and 14 are translated, a series of x-ray attenuation measurements are made through the patient and the resulting set of data provides a transmission profile at one angular orientation. The angular orientation of the devices 13 and 14 is then changed (for example, 1°) and another view is acquired. An alternative structure for acquiring each transmission profile is shown in FIG. 2B. In this construction, the x-ray source 13 produces a fan-shaped beam which passes through the patient and impinges on an array of detectors 14. Each detector 14 in this array produces a separate attenuation signal and the signals from all the detectors 14 are separately acquired to produce the transmission profile for the indicated angular orientation. As in the first structure, the x-ray source 13 and detector array 14 are then revolved to a different angular orientation and the next transmission profile is acquired.

As the data is acquired for each transmission profile, the signals are filtered, corrected and digitized for storage in a computer memory. These steps are referred to in the art collectively as "preprocessing" and they are performed in real time as the data is being acquired. The acquired transmission profiles are then used to reconstruct an image which indicates the x-ray attenuation coefficient of each voxel in the reconstruction field of view. These attenuation coefficients are converted to integers called "CT numbers", which are used to control the brightness of a corresponding pixel on a CRT display. An image which reveals the anatomical structures in a slice taken through the patient is thus produced.

The reconstruction of an image from the stored transmission profiles requires considerable computation and cannot be accomplished in real time. The prevailing method for reconstructing images is referred to in the art as the filtered back projection technique.

Referring to FIG. 3, the proper reconstruction of an image requires that the x-ray attenuation values in each view pass through all of the objects located in the aperture 11. If the object is larger than the acquired field of view, it will attenuate the values in some transmission profiles as shown by the vertically oriented view in FIG. 3, which encompasses the supporting table 10, and it will not attenuate the values in other transmission profiles as shown by the horizontally oriented view in FIG. 3. As a result, when all of the transmission profiles are back projected to determine the CT number of each voxel in the reconstructed field of view, the CT numbers will not be accurate. This inaccuracy caused by truncated projection data can be seen in the displayed image as background shading which can increase the brightness or darkness sufficiently to obscure anatomical details.

A similar problem is presented when transmission profiles are affected by metal objects such as dental filings in the patient being scanned. In this situation x-rays passing through the metal object are strongly absorbed and the attenuation measurement is very noisy causing strong artifacts in the reconstructed image.

The data truncation problem and the x-ray absorption problem each corrupt the acquired attenuation data set in a unique way. Referring to FIG. 4, as views of the attenuation data are acquired the attenuation values 32 in each view are stored on one row of a two dimensional data array 33. As indicated by the dashed line 34, each such row of attenuation data provides a transmission profile of the object to be imaged when viewed from a single view angle. One dimension of the data array 33 is determined by the number of views which are acquired during the scan and the other dimension is determined by the number of detector cell signals acquired in each view.

Referring particularly to FIG. 5, the truncated data problem can be visualized as a set of contiguous views 36 in the acquired data array 33 that are corrupted because they include attenuation information from objects (e.g., supporting table, patient's shoulder or arms) outside the field of view of all the remaining acquired views. On the other hand, as shown in FIG. 6 the absorbed x-ray problem can be visualized as the corruption of one or more attenuation values in all, or nearly all the acquired views as indicated at 38. In the first problem a select few of the acquired views are significantly affected and in the second problem all or nearly all the acquired views are affected in a more limited manner.

The in-plane resolution of a tomographic image reconstructed from divergent beam projection views is dictated by the amount of data acquired during the scan. In-plane resolution can be increased by acquiring additional views at more closely spaced view angles. However, this strategy results in a longer scan time since it requires a finite amount of time to acquire each view. In-plane resolution can also be increased by decreasing the size of each element in the detector array. However, this results in an increase in the number of required detector elements to span the same fan beam angle and the supporting electronics with a consequent increase in scanner cost.

There are a number of situations that result in the corruption of acquired divergent beam projection views. These include subject motion during part of the scan, cardiac motion of the beating heart, and respiratory motion during breathing or an imperfect breathhold.

There are a number of situations that result in the corruption of acquired divergent beam projection views when different energy x-ray beams are utilized in CT imaging. One such example is CT imaging using two different energies of x-ray (80 kVp/140 kVp) in diagnostic dual energy imaging and another example is kV-MV dual energy CT image guided radiation therapy (100 kVp/3000 kVp).

SUMMARY OF THE INVENTION

The present invention is a method for correcting individual attenuation values in fan-beam projections that have been corrupted. More particularly, the present invention is a method which employs a novel fan-beam data consistency condition to estimate individual attenuation measurements in one fan-beam projection view from attenuation measurements made at the other view angles.

A general object of the invention is to replace corrupted x-ray attenuation data acquired during a scan with attenuation data calculated from other, uncorrupted attenuation data acquired during the scan. The estimated and replaced attenuation data may be one or more entire attenuation profiles as occurs when correcting data truncation problems, or it may be selected attenuation values in one or more attenuation profiles as occurs when correcting x-ray absorption problems.

Another general object of the invention is to increase the in-plane resolution of images produced by a divergent beam medical imaging system. Rather than replace corrupted data using the present invention, new projection data may be calculated using the acquired projection views. Additional projection views may be calculated to reduce the angle between views, or additional data may be calculated for each of the acquired projection views to increase the resolution of each projection view.

The present invention alters the trade-off made between image resolution on the one hand and scan time on the other hand. It should be apparent that rather than increasing in-plane image resolution the present invention may also be used to reduce the x-ray dose in a CT system. That is, an image of the same resolution can be reconstructed with fewer acquired projection views thus shortening the scan and reducing x-ray dose.

GENERAL DESCRIPTION OF THE INVENTION

It is well known that if all the projection data are summed in one view of non-truncated parallel-beam projections, the result is a view angle independent constant. Mathematically, this is a special case (zero-order moment) of the so-called Helgason-Ludwig consistency condition on two-dimensional Radon transforms. Physically, this condition states that the integral of the attenuation coefficients over the whole transmission profile should be a view angle independent constant. This data consistency condition (DCC) plays an important role in correcting the X-ray CT image artifacts when some projection data are missing in parallel beam scans. In practice, this may happen when a portion of a scanned object is positioned outside the scan field-of-view (FOV) defined by a CT scanner.

A novel data consistency condition is derived here which enables estimation of attenuation values for fan-beam projections. It will be called a fan-beam data consistency condition (FDCC). The new FDCC explicitly gives an estimation of the projection data for a specific ray by filtering all the available fan-beam projections twice. To derive the FDCC, the following definition of a fan-beam projection $g[\vec{r}, \vec{y}(t)]$ is used as the starting point $$g[\vec{r}, \vec{y}(t)] = \int_0^\infty ds f[\vec{y}(t) + s\vec{r}]. \qquad (1)$$

Figure 7:
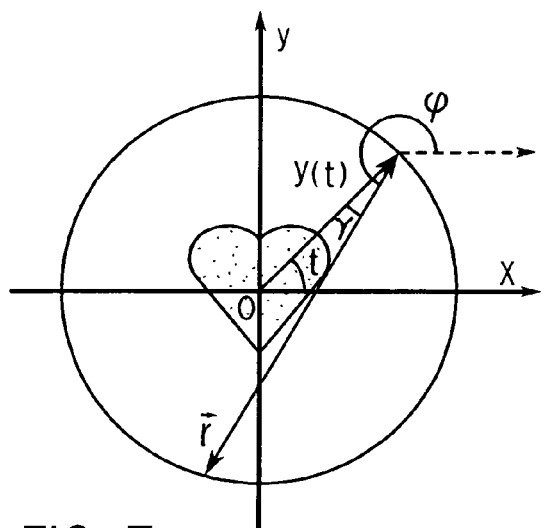
FIG. 7 is a graphic representation of an x-ray beam scan which shows the geometric parameters used to derive data consistency condition.

The source trajectory vector $\vec{y}(t)$ is parameterized by a parameter t, and $\vec{r}$ is a vector starting from the source position to the image object as shown in FIG. 7. The vector $\vec{y}(t)$ denotes a source position and the vector $\vec{r}$ represents a vector from the x-ray source to the imaged object. In a laboratory coordinate system o-xy, the vector $\vec{y}(t)$ is parameterized by a polar angle t, and the vector $\vec{r}$ is parameterized by polar angle $\phi$. The fan angle $\gamma$ is also defined from the iso-ray. All the angles have been defined according to a counterclockwise convention. The image function $f(\vec{x})$ is assumed to have a compact support $\Omega$, i.e., it is non-zero only in a finite spatial region. Throughout this discussion, a vector will be decomposed into its magnitude and a unit vector, e.g. $\vec{r}=r\hat{r}$. Although a circular scanning geometry is shown in FIG. 7, the present invention may be employed in any geometry and a general vector notation is used herein to reflect this fact.

Eq. (1) defines a homogeneous extension of the conventional fan-beam projections $\bar{g}[\hat{r}, \vec{y}(t)]$. That is $$g[\vec{r}, \vec{y}(t)] = \frac{1}{r}\bar{g}[\hat{r}, \vec{y}(t)] = \frac{1}{r}\int_0^\infty ds f[\vec{y}(t) + s\hat{r}]. \quad (2)$$

A Fourier transform $G[\vec{k}, \vec{y}(t)]$ of the generalized fan-beam projection $g[\vec{r}, \vec{y}(t)]$ with respect to variable $\vec{r}$ is defined as $$G[\vec{k}, \vec{y}(t)] = \int_{R^2} d^2 r g[\vec{r}, \vec{y}(t)]\exp(-2\pi i \vec{k} \cdot \vec{r}). \quad (3)$$

Note that this Fourier transform is local, since the Fourier transform is taken with respect to the vectors that emanate from a source position labeled by $\vec{y}(t)$.

By choosing a separate polar coordinate system for vectors $\vec{k}$ and $\vec{r}$ and using Eq. (2), the Fourier transform $G[\vec{k}, \vec{y}(t)]$ can be factorized into the product of a divergent radial component $$\frac{1}{k}$$

and an angular component $\bar{G}[\hat{k}, \vec{y}(t)]$. That is $$G[\vec{k}, \vec{y}(t)] = \frac{1}{k}\bar{G}[\hat{k}, \vec{y}(t)]. \quad (4)$$

Here $\bar{G}[\hat{k}, \vec{y}(t)]$ is similarly defined by Eq. (3), but the vector $\vec{k}$ is replaced by a unit vector $\hat{k}$.

A connection between $G[\vec{k}, \vec{y}(t)]$ and the Fourier transform $\tilde{f}(\vec{k})$ of the object function $f(\vec{x})$ can be established by inserting Eq. (1) and Eq. (2) into Eq. (3). The result is $$G[\vec{k}, \vec{y}(t)] = \frac{1}{k}\int_0^\infty ds \tilde{f}(s\hat{k})\exp[i2\pi s\hat{k} \cdot \vec{y}(t)]. \quad (5)$$

Compared to Eq. (4), the angular component $\bar{G}[\hat{k}, \vec{y}(t)]$ is given by $$\bar{G}[\hat{k}, \vec{y}(t)] = \int_0^\infty dk \tilde{f}(k\hat{k})\exp[i2\pi k\hat{k} \cdot \vec{y}(t)] \quad (6)$$

The presence of the integral in Eq. (6) indicates that the function $\bar{G}[\hat{k}, \vec{y}(t)]$ does not explicitly depend on the vector $\vec{y}(t)$. Rather, the function $\bar{G}[\hat{k}, \vec{y}(t)]$ depends directly on the projection of vector $\vec{y}(t)$ onto a given unit vector $\hat{k}$. Therefore, it is appropriate to introduce a new variable $$p=\hat{k}\cdot\vec{y}(t), \quad (7)$$

and rebin the data $\bar{G}[\hat{k}, \vec{y}(t)]$ into $G_r(\hat{k},p)$ by the following relation $$\bar{G}[\hat{k}, \vec{y}(t)]=G_r(\hat{k},p=\hat{k}\cdot\vec{y}(t)). \quad (8)$$

Using Eqs. (7) and (8), Eq. (6) can be rewritten as $$G_r(\hat{k}, p) = \int_0^\infty dk \tilde{f}(k\hat{k})\exp(i2\pi kp) \quad (9)$$

From the definition given in Eq. (3), it is apparent that the function $G_r(\hat{k},p)$ is a complex function, and thus has both an imaginary part and a real part. In general, the imaginary part and the real part of the function $G_r(\hat{k},p)$ are not correlated with one another. However, Eq. (9) imposes a strong constraint relating the imaginary and real parts of the function $G_r(\hat{k},p)$. To better understand this hidden constraint, the following fact is insightful. The variable k is the magnitude of the vector $\vec{k}$, and thus it is intrinsically a non-negative number. Using this property, Eq. (9) may be extended to the range of $(-\infty,+\infty)$ by introducing a following function $$Q(\hat{k}, k) = \begin{cases} \tilde{f}(k\hat{k}) & k \geq 0 \\ 0 & k < 0 \end{cases} \quad (10)$$

In other words, function $Q(\hat{k},k)$ is a causal function with respect to the variable k. Using the function $Q(\hat{k},k)$, Eq. (9) can be written as:

$$G_r(\hat{k}, p) = \int_{-\infty}^{+\infty} dk Q(\hat{k}, k)\exp(i2\pi pk) \quad (11)$$

Therefore, a standard inverse Fourier transforms yields:

$$Q(\hat{k}, k) = \int_{-\infty}^{+\infty} dp G_r(\hat{k}, p)\exp(-i2\pi pk) \quad (12)$$

Figure 8:
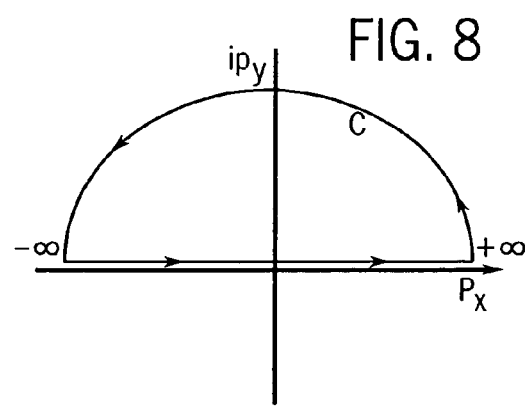
FIG. 8 is a graphic representation used in the derivation of the data consistency condition.

Note that function $Q(\hat{k},k)$ satisfies the causal structure dictated by Eq. (10). This fact implies that, for negative k, the integral in Eq. (12) should universally converge and that the value of the integral should be zero. Therefore, the integral must be done in the upper half of the complex p-plane. In addition, according to a known mathematical theorem, the causal structure in Eq. (10) and (12) requires the function $G_r(\hat{k},p)$ to be analytical in the upper half of the complex p-plane. An intuitive argument is also beneficial in order to demonstrate that the function $G_r(\hat{k},p)$ is analytical in the upper half of the complex p-plane. For negative k, the contour of integration for Eq. (12) should be closed by a large semicircle that encloses the upper half of the complex plane as shown in FIG. 8. By Cauchy's theorem, the integral will vanish if $G_r(\hat{k},p)$ is analytic everywhere in the upper half plane. Thus, the intuitive argument also leads to the conclusion that the function $G_r(\hat{k},p)$ is analytical in the upper half of the complex p-plane.

The complex function $G_r(\hat{k},p)$ may be separated into a real part and an imaginary part as $$G_r(\hat{k},p) = ReG_r(\hat{k},p) + iImG_r(\hat{k},p). \quad (13)$$

The causal structure implied in Eq. (10) and the concomitant analytical structure shown in FIG. 8 require that the real part and imaginary part of the function $G_r(\hat{k},p)$ are mutually linked in the following way:

$$\operatorname{Re} G_r(\hat{k}, p) = \frac{1}{\pi} \wp \int_{-\infty}^{+\infty} dp' \frac{\operatorname{Im} G_r(\hat{k}, p')}{p' - p} \quad (14a)$$

$$\operatorname{Im} G_r(\hat{k}, p) = -\frac{1}{\pi} \wp \int_{-\infty}^{+\infty} dp' \frac{\operatorname{Re} G_r(\hat{k}, p')}{p' - p}, \quad (14b)$$

where the symbol $\wp$ represents Cauchy principal value. In other words, the imaginary part and real part of the function $G_r(\hat{k},p)$ are related to each other by a Hilbert transform.

The imaginary part and real part of function $\overline{G}[\hat{k}, \vec{y}(t)]$ have been explicitly calculated. The final results are $$\operatorname{Re} \overline{G}[\hat{k}, \vec{y}(t)] = \frac{1}{2} \int_0^{2\pi} d\varphi \delta(\hat{k} \cdot \hat{r}) \overline{g}[\hat{r}, \vec{y}(t)] \quad (15)$$

$$\operatorname{Im} \overline{G}[\hat{k}, \vec{y}(t)] = -\frac{1}{2\pi} \int_0^{2\pi} d\varphi \frac{\overline{g}[\hat{r}, \vec{y}(t)]}{\hat{k} \cdot \hat{r}}. \quad (16)$$

Figure 9:
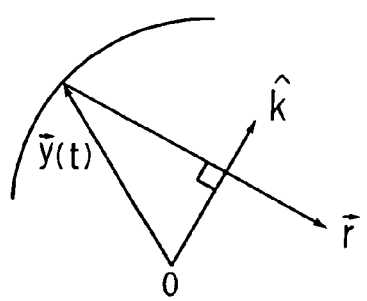
FIG. 9 is a graphic representation showing the relationship of vectors.

Here the angular variable $\phi$ is the azimuthal angle of the unit vector $\hat{r}$, i.e., $\hat{r}=(\cos \phi, \sin \phi)$. An important observation is that there is a Dirac $\delta$-function in Eq. (15). As shown in FIG. 9, for a given unit vector $\hat{k}$ and source position $\vec{y}(t)$, the real part $\operatorname{Re}\overline{G}[\hat{k}, \vec{y}(t)]$ is completely determined by a single ray along the direction $\hat{r}=\hat{k}^\perp$. Note that the clockwise convention has been chosen to define the unit vector $\hat{r}$ from a given unit vector $\hat{k}$. Thus, the real part is given by:

$$\operatorname{Re} \overline{G}[\hat{k}, \vec{y}(t)] = \frac{1}{2}\overline{g}[\hat{r} = \hat{k}^\perp, \vec{y}(t)] = \operatorname{Re} G_r(\hat{k}, p = \hat{k} \cdot \vec{y}(t)) \quad (17)$$

This equation can also be written as $$\overline{g}[\hat{r}, \vec{y}(t)] = 2ReG_r(\hat{k}=\hat{r}^\perp, p=\hat{r}^\perp \cdot \vec{y}(t)) \quad (18)$$

Using equation (14) and equation (16), the following consistency condition on the fan-beam projection data may be derived $$\overline{g}[\hat{r}_0, \vec{y}(t_0)] = \frac{2}{\pi} \wp \int_{-\infty}^{+\infty} dp' \frac{\operatorname{Im} G_r(\hat{r}_0^\perp, p')}{p' - \hat{r}_0^\perp \cdot \vec{y}(t_0)} \quad (19)$$

$$\operatorname{Im} G_r(\hat{r}_0^\perp, p' = \hat{r}_0^\perp \cdot \vec{y}(t)) = -\frac{1}{2\pi} \int_0^{2\pi} d\varphi \frac{\overline{g}[\hat{r}, \vec{y}(t)]}{\hat{r}_0^\perp \cdot \hat{r}}. \quad (20)$$

In order to obtain one specific attenuation profile of projection data $\overline{g}[\hat{r}_0, \vec{y}(t_0)]$ from equation (19), all the possible values of $ImG_r(\hat{k},p)$ are required at the specific orientation $\hat{k}=\hat{r}_0^\perp$. Therefore, it is important to have a scanning path that fulfills at least the short-scan requirement, viz. angular coverage of the source trajectory of 180°+fan angle. Thus, an individual projection at a specific view angle is linked to the projection data measured from all the different view angles via Eqs. (19) and (20). In other words, an individual attenuation profile can be estimated from all the available projection data.

Although equation (19) formally requires all the values of the function Im $G_r(\hat{k},p)$ over the range $p\in(-\infty, +\infty)$, the following modified Hilbert transform may be used to calculate the projection data $\overline{g}[\hat{r}_0, \vec{y}(t_0)]$ using the data of Im $G_r(\hat{k},p)$ over a finite range of $p\in(-A, +A)$ $$\overline{g}[\hat{r}_0, \vec{y}(t_0)] = \frac{2}{\pi\sqrt{A^2 - [\hat{r}_0^\perp \cdot \vec{y}(t_0)]^2}} \times \left[ \frac{\int_{-A}^{+A} dp' \sqrt{A^2 - p'^2}}{\frac{\operatorname{Im} G_r(\hat{r}_0^\perp, p')}{p' - \hat{r}_0^\perp \cdot \vec{y}(t_o)}} + c \right] \quad (21)$$

This formula is mathematically exact when the image object is compactly supported and A is larger than the linear length of the function support. For convenience, a symmetric range has been chosen for the integral, for a more general choice of a nonsymmetric integral range, reference is made to a textbook on integral equations, such as S. G. Mikhlin, Integral Equations And Their Applications To Certain Problems In Mechanics, Mathematical Physics, and Technology (Pergamon N.Y., 1957). In equation (21), the constant c may be determined using a priori knowledge that the projection value is zero outside the compactly supported image object. In addition, the physical range of the parameter p is limited by a scanning path via the definition: $p=\hat{k}\cdot\vec{y}(t)$. Thus the range parameter A in equation (21) should be chosen to be smaller than the gantry radius R for a circular scanning path. Since the range parameter A should be larger than the linear length of the function support, a scanning path that fulfills the short-scan requirement 180°+fan angle, is sufficient to provide physical information for equation (21).

In summary, an individual projection at a specific view angle is linked to the projection data measured from all the other view angles by equations (20) and (21). In other words, an individual projection can be estimated or corrected using available projection data acquired at other view angles.

DESCRIPTION OF THE PREFERRED EMBODIMENT

Figure 10:
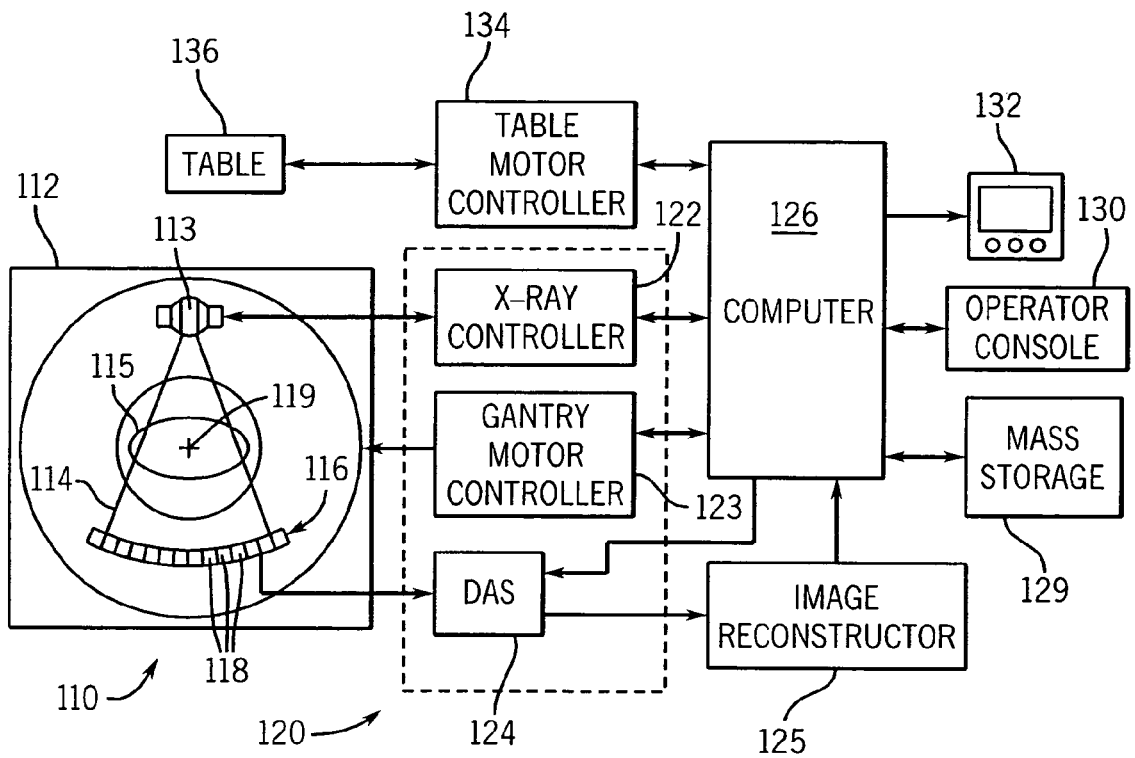
FIG. 10 is a block diagram of a preferred embodiment of an x-ray CT system which employs the present invention.

With initial reference to FIG. 10, a computed tomography (CT) imaging system 110 includes a gantry 112 representative of a "third generation" CT scanner. Gantry 112 has an x-ray source 113 that projects a fan-beam of x-rays 114 toward a detector array 116 on the opposite side of the gantry. The detector array 116 is formed by a number of detector elements 118 which together sense the projected x-rays that pass through a medical patient 115. Each detector element 118 produces an electrical signal that represents the intensity of an impinging x-ray beam and hence the attenuation of the beam as it passes through the patient. During a scan to acquire x-ray projection data, the gantry 112 and the components mounted thereon rotate about a center of rotation 119 located within the patient 115.

The rotation of the gantry and the operation of the x-ray source 113 are governed by a control mechanism 120 of the CT system. The control mechanism 120 includes an x-ray controller 122 that provides power and timing signals to the x-ray source 113 and a gantry motor controller 123 that controls the rotational speed and position of the gantry 112. A data acquisition system (DAS) 124 in the control mechanism 120 samples analog data from detector elements 18 and converts the data to digital signals for subsequent processing. An image reconstructor 125, receives sampled and digitized x-ray data from the DAS 124 and performs high speed image reconstruction according to the method of the present invention. The reconstructed image is applied as an input to a computer 126 which stores the image in a mass storage device 129.

The computer 126 also receives commands and scanning parameters from an operator via console 130 that has a keyboard. An associated cathode ray tube display 132 allows the operator to observe the reconstructed image and other data from the computer 126. The operator supplied commands and parameters are used by the computer 126 to provide control signals and information to the DAS 124, the x-ray controller 122 and the gantry motor controller 123. In addition, computer 126 operates a table motor controller 134 which controls a motorized table 136 to position the patient 115 in the gantry 112.

The fan-beam data consistency condition (FDCC) derived generally above is applied to this preferred geometry by restricting the motion of the x-ray source $\vec{y}(t)$ to a circle centered at the origin "0" with a radius R. The scanning path is parameterized by a polar angle t shown in FIG. 7. Therefore, we have the following parameterization of the source trajectory $$\vec{y}(t) = R(\cos t, \sin t). \tag{22}$$

In addition, it is also useful to consider the following parameterizations for the unit vectors $\hat{r}$, $\hat{r}_0$, and $\hat{r}_0^\perp$ in the laboratory coordinate system:

$$\hat{r} = (\cos \phi, \sin \phi), \tag{23}$$

$$\hat{r}_0 = (\cos \phi_0, \sin \phi_0), \tag{24}$$

$$\hat{r}_0^\perp = (-\sin \phi_0, \cos \phi_0) \tag{25}$$

For convenience, the notation $g_m(\gamma,t)$ is used to describe the measured fan-beam projections with an equi-angular curved detector. The projection angle $\gamma$ is in the range $$[-\frac{\gamma_m}{2}, \frac{\gamma_m}{2}]$$

where $\gamma_m$ is the fan angle. By definition, $$g_m(\gamma,t) = \bar{g}[\hat{r}, \vec{y}(t)] \tag{26}$$

with the following relation between $\phi$ and $\gamma$ $$\phi = \pi + t + \gamma \tag{27}$$

In practice, it is beneficial to introduce the following definitions:

$$ImG_r(\hat{r}_0^\perp, p') = F_p(\phi_0, p') = F_t(\phi_0, t) \tag{28}$$

$$p' = \hat{r}_0^\perp \cdot \vec{y}(t) = R \sin(t - \phi_0) \tag{29}$$

$$\phi_0 = \pi + t_0 + \gamma_0 \tag{30}$$

In the second equality in equation (28), a data rebinning has been introduced using equation (29).

Using these definitions, equations (21) and (20) for this geometry may be expressed as follows:

$$g_m(\gamma_0, t_0) = \frac{2}{\pi\sqrt{A^2 - p_0^2}} \left[ \int_{-A}^{+A} dp' \frac{\sqrt{A^2 - p'^2}}{p' - p_0} F_p(\phi_0, p') + c \right] \text{ and} \tag{31}$$

$$F_p(\phi_0, p') = F_t(\phi_0, t) \tag{32}$$

$$= \frac{1}{2\pi} \int_{-\gamma_m/2}^{+\gamma_m/2} d\gamma \frac{1}{\sin(\phi_0 - t - \gamma)} g_m(\gamma, t),$$

where the number $p_0$ and c in equation (31) are given by:

$$p_0 = R \sin \gamma_0. \tag{33}$$

$$c = -\int_{-A}^{+A} dp' \frac{\sqrt{A^2 - p'^2}}{p' - \overline{p_0}} F_p(\phi_0, p'). \tag{34}$$

In equation (34), the parameter $\overline{p_0}$ is a number smaller than A, but it is still large enough to be outside the function support. Equations (31) and (32) explicitly relate a single projection to the other measured projection data for all the view angles. Given a desired projection view labeled by parameters $\gamma_0$ and $t_0$, the numerical procedure to achieve this specific projection view may be summarized in the following steps:

Step 1: For each view angle, filter the measured data by a filtering kernel $1/\sin \gamma$ to obtain $F_t(\phi_0, t)$.

Step 2: Rebin the filtered data $F_t(\phi_0, t)$ into $F_p(\phi_0, p')$ in equation (29).

Step 3: Filter the rebinned data $F_p(\phi_0, p')$ again using a finite range Hilbert transform (????) and linearly interpolate to obtain the value $p_0 = R \sin \gamma_0$ which corresponds to the projection data $g_m(\gamma_0, t_0)$.

Figure 5:
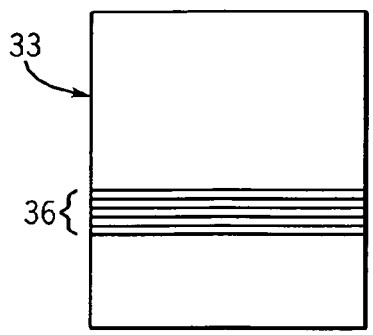
FIG. 5 is a pictorial representations of the data array of FIG. 4 illustrating data that may be corrupted by one problem encountered when scanning subjects with the system of FIG. 1.
Figure 6:
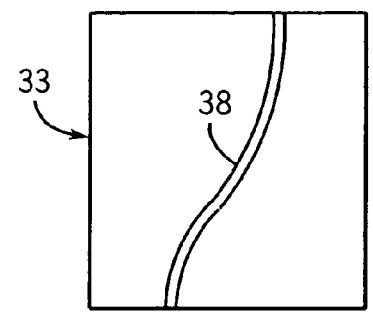
FIG. 6 is a pictorial representation of the data array of FIG. 4 illustrating data that may be corrupted by a second problem encountered when scanning subjects.
Figure 11:
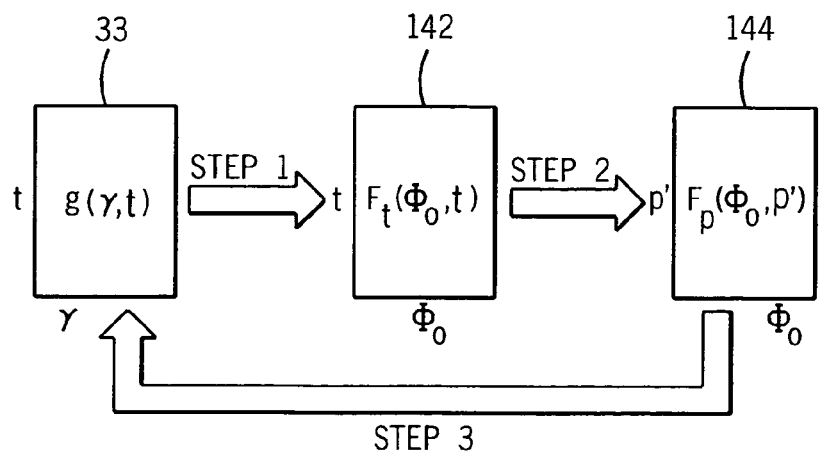
FIG. 11 is a pictorial representation of the data structures that are produced when practicing the steps of the present invention.

This process is implemented by a program executed by the computer 126 after the scan is completed and the acquired attenuation data $g_m(\gamma, t)$ is stored in data array 33. As shown in FIG. 11, the above step 1 is performed on the entire data set 140 to produce data set $F_t(\phi_0, t)$ which is stored as array 142. This data set is rebinned as described above in step 2 to form $F_p(\phi_0, p')$ which is stored in data array 144. The attenuation values $g_m(\gamma_0, t_0)$ at any view angle $t_0$ can then be estimated using the data in array 144 and Eq. (31) as described above in step 3. It can be appreciated that any acquired attenuation profile can be estimated in this manner in its entirety, or only a particular attenuation value therein may be estimated. Thus, in the truncated data problem illustrated in FIG. 5A, the views 36 in the acquired data array 33 are replaced with estimated values, whereas in the absorbed x-ray problem illustrated in FIG. 5B, the corrupted attenuation values 38 in the data array 33 are replaced with estimated values.

It should be apparent that the method can be repeated using the corrected attenuation data in array 33 to further improve the results. Such an iterative process is normally not necessary when only a small amount of the acquired data is corrupted, but further iterations are required as the proportion of corrupted data increases.

Another application of the present invention is to correct acquired divergent beam projection views for subject motion during the scan. As with the embodiments discussed above, the corrupted projection views are identified and the present invention is employed to calculate new projection views to replace the corrupted views. The uncorrupted projection views are used to make the calculations. If a large number of views are corrupted the calculations may be repeated a number of times. The repeated calculations use both the uncorrupted originally acquired projection views plus the calculated replacement views in an iterative process that converges to the best estimate for the replacement projection views.

The present invention may also be used to optimize all of the acquired projection views. This may be done, for example, to improve beam hardening adjustments made to each projection view. In this application each acquired projection view is recalculated using all of the other acquired projection views in accordance with the present invention. This may be repeated a number of times so that the resulting set of modified projection views are adjusted to make them consistent attenuation measurements at all view angles.

The present invention may also be used to improve image quality in multisource CT imaging. This may be done, for example, to calculate and compensate for the missing projection data when one x-ray source only generates x-ray projection data to cover part of the image object while the other x-ray source generates x-ray projection data to cover the whole image object.

The present invention may also be used to improve image quality in multi-energy CT imaging. This may be down, for example, to calculate projection data for a given energy (e.g., 100 kV) from the projection data acquired at a different energy (e.g., 3 MV).

Figure 1:
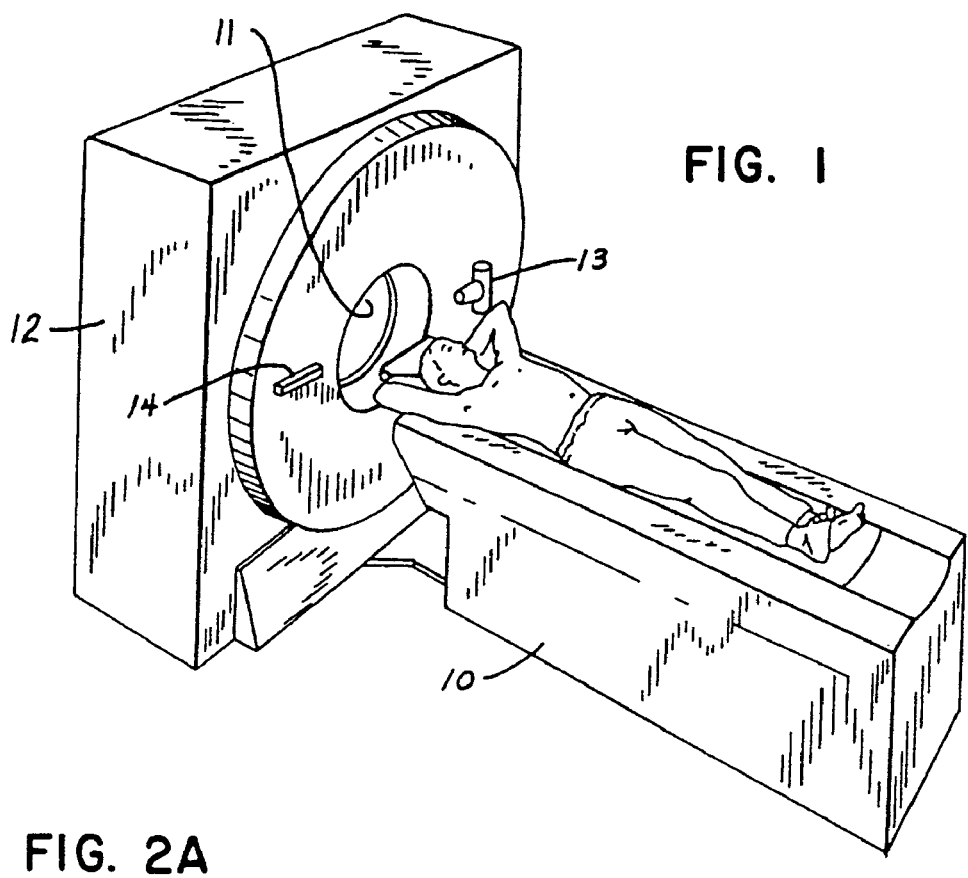
FIG. 1 is a perspective view of an x-ray CT system which employs the present invention.
Figure 2A:
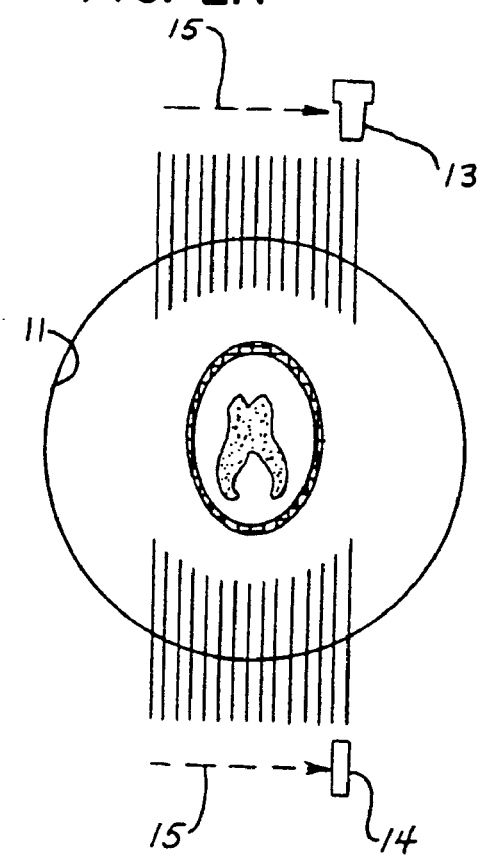
FIGS. 2A and 2B are pictorial representations of a parallel beam and fan-beam scan respectively that may be performed with a CT system.
Figure 2B:
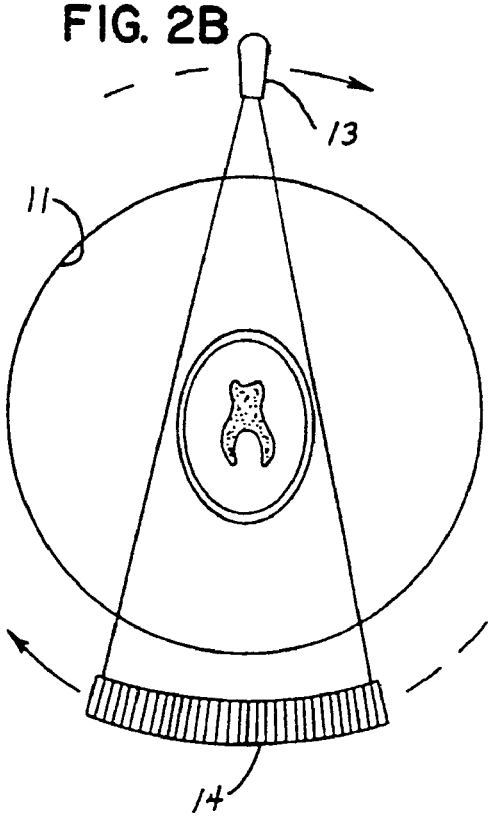
Figure 3:
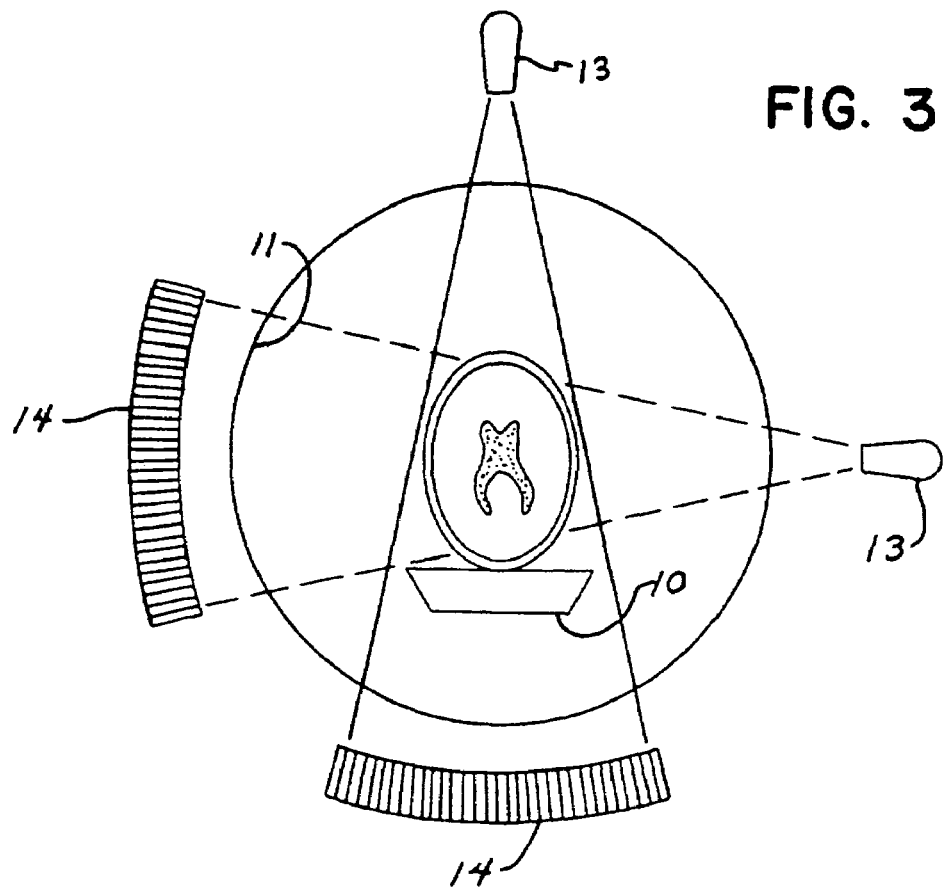
FIG. 3 is a pictorial representation of a fan-beam acquisition situation which results in a data truncation problem that is solved using the present invention.
Figure 4:
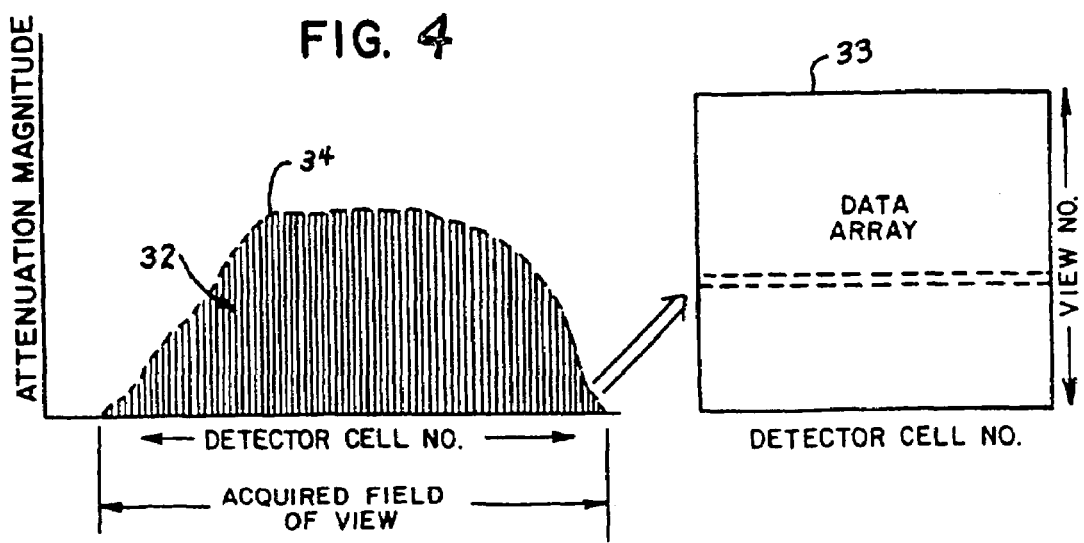
FIG. 4 is a pictorial representation of an attenuation profile acquired by the system of FIG. 1 and its storage in a data array.
Figure 12:
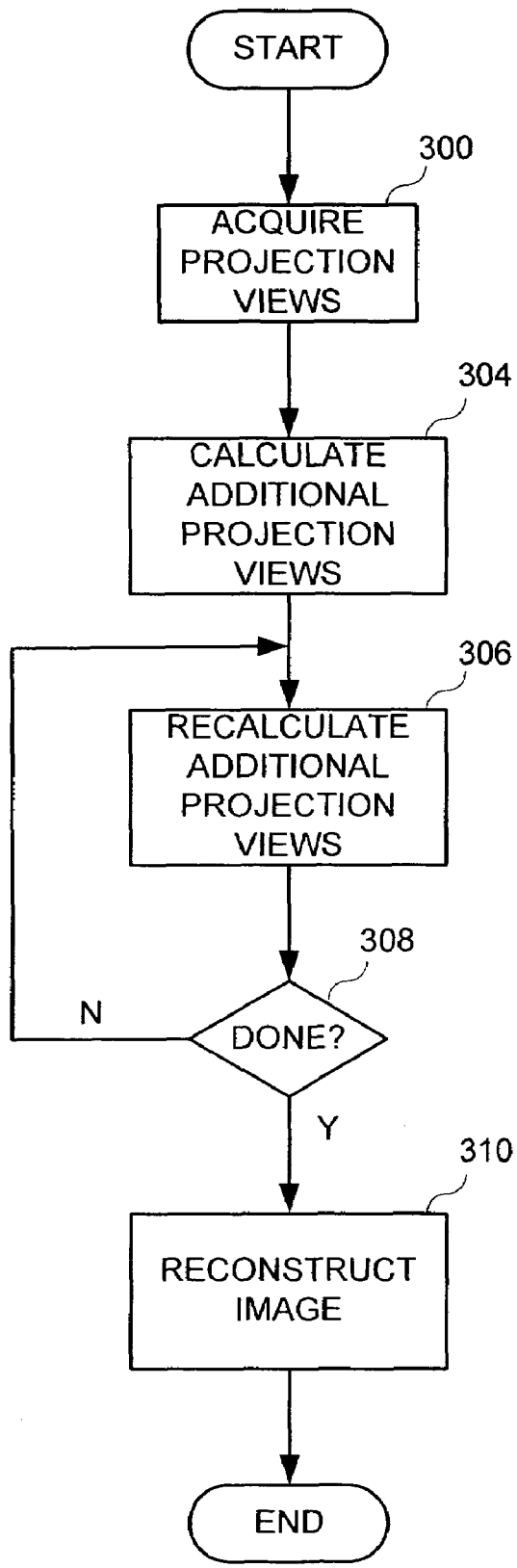
FIG. 12 is a flow chart of another embodiment of the invention practiced on the CT system of FIG. 1.
Figure 13:
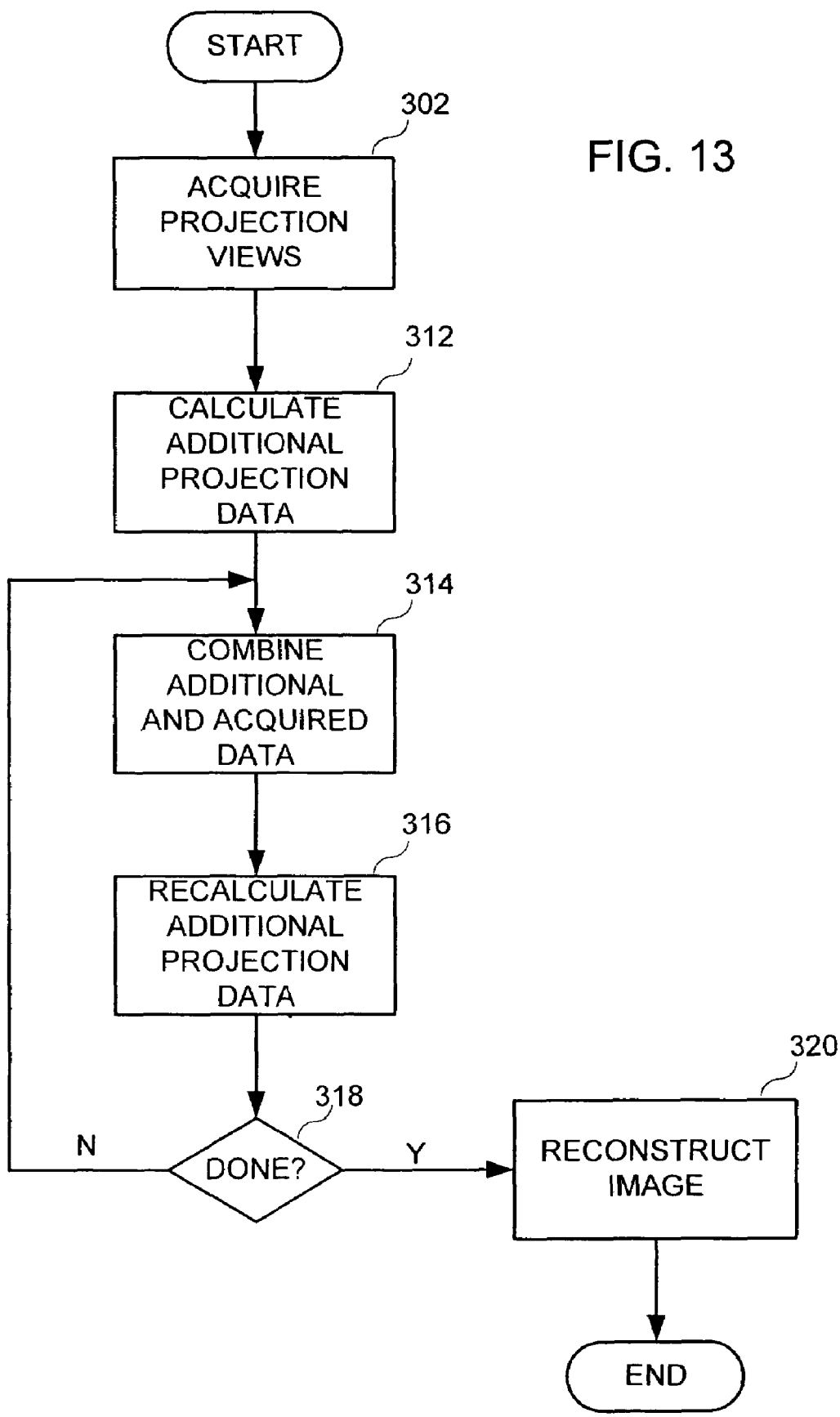
FIG. 13 is a flow chart of yet another embodiment of the invention practiced on the CT system of FIG. 1.

The present invention may also be used to increase the in-plane resolution of a tomographic scanner. This can be done in either or both of two ways. Referring particularly to FIGS. 4, 12 and 13 during the scan a set of projection views are acquired as indicated at process block 300 and 302 to form a data set 33 of a prescribed size. Using this acquired data set the resolution of the image that may be reconstructed is dictated by the number of views acquired within the range of view angels and the number of detector cell signals in each view. In the embodiment of FIG. 12 the potential image resolution is increased by calculating additional projection views as indicated at process block 304. The above equations are employed to make this calculation using all the acquired projection views. These additional views are interleaved with the acquired views to reduce by one-half the angle between adjacent views. Referring again to FIG. 4, this doubles the number of views in the data set 33 to enable a doubling of the resolution of the reconstructed image.

Referring again to FIG. 12, because of the large number of estimated views added to the acquired projection views it is necessary to repeat the calculations to improve accuracy. As indicated at process block 306 all of the additional, estimated projection views are recalculated, but this time the calculations are performed with the previously calculated estimated projection views along with the originally acquired projection views. As indicated at decision block 308 a determination is made as to whether additional iterations are required or whether the processing is completed. The criteria used to make this determination will vary depending on the particular application, but four iterations has been found sufficient in most cases. When the additional projection views are suitably estimated, the combined acquired and calculated projection views are used to reconstruct an image as indicated at process block 310. This step uses a conventional filtered back projection method.

Referring particularly to FIG. 13, another method which uses the present invention to increase image resolution creates additional, interleaved projection measurements in each acquired projection view. Referring to FIG. 4, this effectively increases the number of detector elements in the data array 33. As indicated at process block 312, the additional projection data is calculated by first estimating the additional values. This is done in the preferred embodiment by interpolating between the values of the adjacent detector elements in the array 33. These are the projection values at the closest angles to the desired projection angle. After the additional values have been estimated through interpolation the present invention is employed to calculate the additional projection values. This is done using all the projection views with both acquired and estimated projection data in each view.

Because a significant amount of additional data is estimated, the calculations are repeated as indicated at process blocks 314 and 316. First the previously calculated, additional projection data in each projection view is combined with the original, acquired projection data for that view as indicated at process block 314. Then, the present invention is used with the newly combined projection data to recalculate each projection view as indicated at process block 316. Since each projection view is recalculated both the additional, estimated projection data and the originally acquired projection data in each view are changed. It is for this reason step 314 is needed for each iteration to re-insert the originally acquired projection data.

When the additional estimated projection data has been recalculated a sufficient number of times as determined at decision block 318, the image is reconstructed as indicated at 320 using the most recently calculated additional projection values and the originally acquired projection values. The additional projection values effectively increase the resolution of the detector without any hardware modification to the imaging system.

It should be apparent that while the direct benefit of the present invention may be to increase in-plane image resolution, this benefit may be traded off to provide other benefits. For example, by reducing the number of originally acquired projection view angles the scan time can be reduced and the x-ray dose delivered to the patient can be reduced. The original image resolution is then restored using the present invention as described above.

It should be apparent from the above description that the present invention is a method for processing acquired projection data used to reconstruct images. As such no change is required in the image acquisition hardware or software and no change is required in the image reconstruction method. The present invention may, therefore, be embodied as a post processing set of tools which may be selectively used to improve an acquired image. For example, an image may be acquired and reconstructed for clinical use and it is observed that the image is corrupted or is not of high enough resolution. The appropriate tool described above can be selected and applied to the acquired image data to replace corrupted data or to calculate additional data for improved image resolution.

While the present invention is described with reference to fan-beam x-ray CT systems, it is also applicable to other divergent beam imaging modalities such as radiation therapy systems, PET scanner and PET/CT systems. Projection data acquired with a fan, or divergent, beam may be estimated using the present invention where projection data is acquired from the same subject at a sufficient number of other projection angles.

The invention claimed is:

1. A method for producing a CT image using an imaging system having a divergent beam, the method comprising:
   a) acquiring an array of measurements with the divergent beam imaging system including projection view measurements at each of a plurality of projection angles;
   b) for each of a plurality of desired values, determining an estimate of the desired value at a corresponding projection angle by:
      i) filtering values in the array with a first filtering kernel;
      ii) rebinning the filtered values; and
      iii) calculating an estimate of the desired value by filtering the rebinned values with a second filtering kernel; and
   c) reconstructing the CT image using the estimated desired values.

2. The method as recited in claim 1 in which the second filtering kernel is a Hilbert kernel.

3. The method as recited in claim 1 in which the first filtering kernel is $1/\sin \gamma$, where $\gamma$ is the projection angle of the divergent beam as measured from the midpoint of the divergent beam.

4. The method as recited in claim 1 in which the estimated desired values each replace a corresponding value acquired with the divergent beam imaging system.

5. The method as recited in claim 1 in which the estimated desired values are calculated at projection angles not measured by the divergent beam imaging system.

6. The method as recited in claim 5 in which the estimated desired values are interleaved with the projection view measurements for reconstruction.

7. A method for increasing the resolution of an image acquired with a CT system having a divergent beam, the steps comprising:
   a) acquiring an array of measurements with the divergent beam imaging system including projection view measurements at each of a plurality of projection angles;
   b) calculating additional array measurements at desired projection angles not acquired in step a), wherein each additional measurement is calculated by:
      i) filtering measurements in the array with a first filtering kernel;
      ii) rebinning the filtered measurements; and
      iii) filtering the rebinned measurements with a second filtering kernel; and
   c) reconstructing an image using the measurements acquired in step a) and the additional array measurements calculated in step b).

8. The method as recited in claim 7 in which step b) is repeated to recalculate the additional array measurements using both measurements acquired in step a) and additional array measurements previously calculated in step b).

9. The method as recited in claim 7 in which the first filtering kernel is $1/\sin \gamma$, where $\gamma$ is the projection angle of the measurement being calculated as measured from the midpoint of the divergent beam.

10. The method as recited in claim 7 in which the second filtering kernel is a Hilbert transform.

11. The method as recited in claim 10 in which the Hilbert transform is a finite range Hilbert transform.

12. A method for producing an image using an imaging system with a divergent beam, the method comprising:
   a) acquiring an array of measurements with the divergent beam imaging system including measurements acquired at different projection angles;
   b) estimating a desired value corresponding to a projection angle using the measurements acquired at other projection angles and data consistency condition; and
   c) reconstructing an image using the estimated desired value and the acquired measurements.

13. The method as recited in claim 12 in which the value estimated in step b) is a value at a projection angle that is not acquired by the imaging system.

14. The method as recited in claim 12 in which the estimated value replaces a corresponding measurement acquired by the imaging system.

15. The method as recited in claim 12 in which step b) is repeated a plurality of times to estimate a corresponding plurality of desired values.

16. The method as recited in claim 12 in which step b) is repeated to recalculate the desired values using both measurements acquired in step a) and values estimated during previous iterations of step b).

17. The method as recited in claim 16 in which step b) includes:
   i) filtering values in the array of measurements with a first filtering kernel;
   ii) rebinning the filtered values; and
   iii) calculating an estimate of a value by filtering the rebinned values with a second filtering kernel.

18. The method as recited in claim 17 in which the first filtering kernel is $1/\sin \gamma$, where $\gamma$ is the projection angle of the divergent beam as measured from the midpoint of the divergent beam.

19. The method as recited in claim 17 in which the second filtering kernel is a Hilbert kernel.

20. The method as recited in claim 17 in which the estimated desired value replaces a value acquired with the imaging system which was corrupted during its acquisition.

* * * * *